United States Patent
Rus et al.

(10) Patent No.: US 10,487,360 B2
(45) Date of Patent: *Nov. 26, 2019

(54) DIAGNOSIS AND PROGNOSIS OF MULTIPLE SCLEROSIS

(71) Applicants: Horea Rus, Catonsville, MD (US); Cornelia Cudrici, Rockville, MD (US); Cosmin Tegla, Bronx, NY (US)

(72) Inventors: Horea Rus, Catonsville, MD (US); Cornelia Cudrici, Rockville, MD (US); Cosmin Tegla, Bronx, NY (US)

(73) Assignees: University of Maryland, Baltimore, Baltimore, MD (US); The Department of Veterans Affairs, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 15/093,456

(22) Filed: Apr. 7, 2016

(65) Prior Publication Data

US 2016/0208332 A1    Jul. 21, 2016

Related U.S. Application Data

(63) Continuation-in-part of application No. 13/774,854, filed on Feb. 22, 2013, now abandoned, which is a continuation-in-part of application No. PCT/US2011/001487, filed on Aug. 24, 2011, now abandoned.

(60) Provisional application No. 61/402,121, filed on Aug. 24, 2010.

(51) Int. Cl.
   *C12Q 1/6883* (2018.01)
   *C12Q 1/68* (2018.01)

(52) U.S. Cl.
   CPC ..... *C12Q 1/6883* (2013.01); *C12Q 2600/106* (2013.01); *C12Q 2600/112* (2013.01); *C12Q 2600/118* (2013.01); *C12Q 2600/158* (2013.01)

(58) Field of Classification Search
   None
   See application file for complete search history.

(56) References Cited

U.S. PATENT DOCUMENTS

2008/0013092 A1* 1/2008 Maltezos .......... G01N 21/6452
                                                356/417

OTHER PUBLICATIONS

Achiron et al. Ann. N.Y. Acad. Sci. 2007. 1107: 155-167.*
Affymetrix. Retrieved on May 2, 2017 from the internet: < https://www.affymetrix.com/analysis/netaffx/showresults.affx#>.*
GeneCards. Retrieved on May 5, 2017 from the internet: http://www.genecards.org/cgi-bin/carddisp.pl?gene=RGCC&keywords=RGC-32.*
Achiron et al. Disease Markers. 2009. 27: 63-73.*
Kruszewski et al. Experimental and Molecular Pathology. 2015. 99:498-505.*
Tegla et al. Experimental and Molecular Pathology. 2013. 94:17-28.*
Sanguine Biosciences. Retrieved on May 2, 2017 from the internet: http://sanguine.wpengine.com/types-of-immune-cells-present-in-human-pbmc/.*
Palmer et al. BMC Genomics. 2006. 7: 115.*

* cited by examiner

*Primary Examiner* — Joseph G. Dauner
(74) *Attorney, Agent, or Firm* — Benjamin Aaron Adler

(57) ABSTRACT

The present invention provides a method for determining whether an individual with relapsing-remitting multiple sclerosis will suffer a relapse or respond to treatment for MS. A ratio of mRNA levels of Response Gene to Complement-32, FasL or IL-21 to L13 determined for an individual provides a normalized level which is compared to a cut-off value. A normalized level of Response Gene to Complement-32 greater than 2.52, a normalized level of FasL greater than 85.4 and a normalized level of IL-21 less than 11.9, respectively, indicates the individual will have or is having a relapse of multiple sclerosis. Also provided are methods for determining whether an individual will respond positively or is responding positively to glatiramer treatment and whether the individual is in a period of stable disease or is not at risk for relapse of multiple sclerosis by comparing normalized levels with the respective cut-off levels.

17 Claims, 8 Drawing Sheets

Specification includes a Sequence Listing.

DIAGNOSIS AND PROGNOSIS OF MULTIPLE SCLEROSIS

CROSS-REFERENCE TO RELATED APPLICATIONS

This application is a continuation-in-part under 35 U.S.C. § 120 of pending application U.S. Ser. No. 13/774,854, filed Feb. 22, 2013, which is a continuation-in-part of international application PCT/US2011/001487, filed Aug. 24, 2011, now abandoned, which claims benefit of priority under 35 U.S.C. § 119(e) of provisional application U.S. Ser. No. 61/402,121, filed Aug. 24, 2010, now abandoned, the entirety of all of which are hereby incorporated by reference.

BACKGROUND OF THE INVENTION

Field of the Invention

The present invention relates to the fields of diagnostic and therapeutic neurology. More specifically, the present invention relates to, inter alia, methods of diagnosis and prognosis in multiple sclerosis.

Description of the Related Art

Progression through each phase of the cell cycle is controlled by specific cyclin dependent kinases (CDK) and their interactions with cyclins and CDK inhibitors (CKI). The expression of each cyclin fluctuates throughout the cell cycle, and CKI are down-regulated in response to mitogenic stimulation. Cyclin dependent kinases are a family of serine/threonine protein kinases that are regulated by multiple mechanisms leading to their activation at specific points of the cell cycle. Mitosis is regulated by CDC2 when in complex with cyclin B. Deregulation of the cell cycle is well documented in cancer, and compounds with CDK inhibitory activity have recently entered clinical trials. The expression of CDC2, CDK2 and CDK4 proteins is higher in colon cancer cells than in normal mucosa. Higher levels of cyclins DI, D3, A and E were also found in primary colorectal carcinomas than in the adjacent normal areas. It is also documented that CDC2 kinase activity is increased in colon cancer tissue, but not in normal tissue. CDC2 is mostly present in colon cancer cells positive for phosphorylated Rb protein, and its overexpression is higher in focal carcinomas. The cyclin dependent pathway is, however, complicated and other factors are necessary for proper function and progression through the cell cycle.

One of these other factors, the Response Gene to Complement (RGC)-32 was first cloned in the rat by differential display (1), and subsequently from human brain library (2). Overexpression of RGC-32 is associated with an increase in DNA synthesis, thus leading to the hypothesis that RGC-32 is involved in activation of the cell cycle (1). Experimental evidence indicates that RGC-32 has an important role in cell cycle activation through regulation of CDC2 kinase (2). Overexpression of RGC-32 in human aortic smooth muscle cells (SMC) increased BrdU incorporation and the number of cells progressing into G2/M phase. RGC-32 appears to complex with CDC2/cyclin BI and increase the kinase activity of CDC2. This kinase-enhancing activity requires CDC2 phosphorylation of RGC-32 at Threonine 91. These findings identify RGC-32 as a substrate and regulator of CDC2.

Thus, the Response Gene to Complement (RGC)-32, acts primarily as a cell cycle regulator (1-2). RGC-32 overexpression leads to an increase in DNA synthesis and cell cycle progression from the G1/G0 to G2/M phase (2). Both of these responses can be abolished by transfecting the cells with RGC-32-specific siRNA (3). RGC-32 forms complexes with CDC2 and enhances CDC2 kinase activity (2). Thus, RGC-32 appears to be a previously unrecognized regulator of CDC2, a critical kinase involved in cell cycle activation.

Multiple sclerosis (MS) is a chronic autoimmune inflammatory disease of the central nervous system and is a common cause of persistent disability in young adults. In patients suffering from MS, the immune system destroys the myelin sheet of axons in the brain and the spinal chord, causing a variety of neurological pathologies. In the most common form of MS, Relapsing-Remitting, episodes of acute worsening of neurological function (exacerbations, attacks) are followed by partial or complete recovery periods (remissions) that are free of disease progression (stable). It has been reported that ninety percent of patients with MS initially present with a clinically isolated syndrome because of an inflammatory demyelinating lesion in the optic nerve, brain stem, or spinal cord. About thirty percent of those patients with a clinically isolated syndrome progress to clinically definite MS within 12 months of presentation. The subsequent progression of the disease can vary significantly from patient to patient. The progression can range from a benign course to a classic relapsing-remitting, chronic progressive, or rare fulminant course.

A method for diagnosing MS that facilitates early MS diagnosis and prediction of disease activity (Benign, Moderate and Malignant) would be valuable for both managing the disease and providing counsel for the patient. For example, patients diagnosed early with active course of MS could be offered disease modifying treatments that have recently been shown to be beneficial in early MS.

Current methods for assessment and tracking progress of MS are based on assessment and scoring of patients' function in attacks and accumulated disabilities during the attacks. One assessment used to assess MS is the Expanded Disability Status Scale (EDSS). However, EDSS score system measures the outcome and does not have predict for the progression of the disease. In addition, EDSS scoring can be variable because it is based on a subjective assessment of patient function. Methods for diagnosis can also include tracking brain lesions by Magnetic Resonance Imaging (MRI) or testing Cerebrospinal Fluid (CSF) for Oligo-Clonal Banding (OCB). MRI is a physical method for assessment of brain lesions and is used widely for MS diagnosis. However, it has only very long term predictive value. In addition, the correlation between MRI results and disease activity is poor. Thus, MRI can not be used for short term projections of disease activity or disease management.

Cerebrospinal puncture is an unpleasant invasive procedure that is not suitable for routine use or prognosis. In addition, both methods assess damage only after it has occurred; neither method can predict the onset of attacks or silent, sub-clinical lesions. A further disadvantage in testing for Oligo-Clonal Banding, e.g., in CSF and MRI as a way to diagnose MS is that a negative Oligo-Clonal Banding or MRI will not preclude the existence of MS.

Most patients with MS initially present with a clinically isolated syndrome (CIS). Despite the fact that MS will develop in up to 80% of these patients, the course of the disease is unpredictable at its onset. The disease may remain inactive for many years before the appearance of a second clinical relapse or new lesions on MRI confirm the diagnosis. Because currently available therapy is only partially effective and side effects are common, many neurologists are uncertain whether to treat all such patients with immunomodulators, or to wait until the diagnosis is confirmed by a second clinical event or the appearance of new MRI lesions.

There is a need for a simple serological assay that predicts whether patients with a CIS suggestive of MS or newly diagnosed relapsing remitting MS will have a highly active disease course and therefore require aggressive treatment, or whether they will follow a more benign course that enables such patients to postpone immunomodulatory therapy until necessary. This assay would be also useful in helping the diagnosis of MS. There is also a need for a method that uses objectively assessed markers for diagnosing MS and for predicting disease activity, the onset of attacks or silent lesions in patients suffering from MS.

Little is currently known about the potential role of RGC-32 in autoimmune disorders, including multiple sclerosis (MS). Several studies have demonstrated impaired apoptosis of T cells in multiple sclerosis patients (4-6). Furthermore, relapses may be associated with the persistent presence of myelin-activated T cells resulting from impaired T-cell apoptosis (4-6). T-cell apoptosis in both experimental allergic encephalomyelitis (EAE) and multiple sclerosis is regulated in part by the Fas-FasL system (6), and ex vivo studies have demonstrated an increased resistance of T cells to Fas-mediated apoptosis during multiple sclerosis relapses (7). In addition, FasL expression has been found to be low during relapses, consistent with the increased resistance of the T cells to apoptosis (8). FasL expression on T cells is regulated by multiple factors, including the CDC2/cyclin B1 complex (9). Since RGC-32 binds to CDC2/cyclin B1 complex and up-regulates its activity, it is possible that RGC-32 is involved in regulating T-cell survival by modulating the expression of FasL. Preliminary studies have shown that RGC-32 is expressed by $CD3^+$ as well as $CD4^+$ T cells from peripheral blood (PB) and in brain tissue from MS patients (10-11).

Thus, there is a continued need in the art for improved methods and therapies to diagnose and treat multiple sclerosis and autoimmune diseases. The present invention fulfills this long standing need and desire in the art.

SUMMARY OF THE INVENTION

The present invention is directed to a method for determining whether an individual with relapsing-remitting multiple sclerosis will suffer a relapse, comprising the step of: measuring the mRNA level of Response Gene to Complement-32 in peripheral blood mononuclear cells of the individual; measuring the mRNA level of L13 in peripheral blood mononuclear cells of the individual; calculating a ratio of the mRNA levels of Response Gene to Complement-32 to the mRNA level of L13 to obtain a normalized level of Response Gene to Complement-32; and comparing the normalized level of Response Gene to Complement-32 to a cut-off value of 1.27, wherein a normalized level of Response Gene to Complement-32 less than 1.27 indicates that the individual will have or is having a relapse of multiple sclerosis.

In another embodiment, the present invention provides a method for determining whether an individual with relapsing-remitting multiple sclerosis will suffer a relapse, comprising the step of: measuring the mRNA level of FasL in peripheral blood mononuclear cells of the individual; measuring the mRNA level of L13 in peripheral blood mononuclear cells of the individual; calculating a ratio of the mRNA levels of FasL to the mRNA level of L13 to obtain a normalized level of FasL; and comparing the normalized level of FasL to a cut-off value of 52.6, wherein a normalized level of FasL less than 52.6 indicates that the individual will have or is having a relapse of multiple sclerosis.

In yet another embodiment, the present invention provides a method for determining whether an individual with relapsing-remitting multiple sclerosis will suffer a relapse, comprising the step of: measuring the mRNA level of IL-21 in peripheral blood mononuclear cells of the individual; measuring the mRNA level of L13 in peripheral blood mononuclear cells of the individual; calculating a ratio of the mRNA levels of IL-21 to the mRNA level of L13 to obtain a normalized level of IL-21; and comparing said normalized level of IL-21 to a cut-off value of 16.9, wherein a normalized level of IL-21 greater than 16.9 indicates that the individual will have or is having a relapse of multiple sclerosis.

In yet another embodiment, the present invention provides a method for determining whether an individual with relapsing-remitting multiple sclerosis will respond positively to glatiramer treatment for multiple sclerosis, comprising the step of: administering the glatiramer treatment to the individual; and measuring the mRNA levels of Response Gene to Complement-32, FasL and IL-21 in peripheral blood mononuclear cells of said individual after the treatment; measuring the mRNA level of L13 in peripheral blood mononuclear cells of the individual; calculating said mRNA levels of Response Gene to Complement-32, FasL and IL-21 by the mRNA level of L13 to obtain normalized levels of Response Gene to Complement-32, FasL and IL-21; and comparing said normalized levels of Response Gene to Complement-32, FasL and IL-21 to a cut-off value of 2.52, wherein a normalized level of Response Gene to Complement-32 greater than 2.52, greater than 85.4 and less than 11.9, respectively in the individual indicates that said individual will respond positively or is responding positively to the treatment.

In yet another embodiment, the present invention provides a method for determining whether an individual with relapsing-remitting multiple sclerosis is in a period of stable disease or is not at risk for relapse of multiple sclerosis, comprising the step of: measuring the mRNA level of Response Gene to Complement-32, FasL and IL-21 in peripheral blood mononuclear cells of the individual for at least two times sequentially; measuring the mRNA level of L13 in peripheral blood mononuclear cells of the individual; calculating the mRNA levels of Response Gene to Complement-32 by the mRNA level of L13 to obtain a normalized level of Response Gene to Complement-32; and comparing the normalized level of Response Gene to Complement-32 to a previous measurement of normalized level of Response Gene to Complement-32, wherein a significantly higher normalized level of Response Gene to Complement-32 than a previous measurement thereof in the individual indicates that the individual is in a period of stable disease or is not at risk for relapse of multiple sclerosis.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1A shows that significantly lower levels of RGC-32 mRNA were found in patients with relapses compared to clinically stable patients ($p<0.0001$). FIG. 1B shows that significantly lower levels of FasL mRNA were found in patients with relapses compared to clinically stable patients ($p<0.0001$). FIGS. 1C-1D show that no statistically significant changes were observed in CDC2 or AKT mRNA. FIG. 1E shows that significantly higher levels of IL-21 mRNA were found in patients with relapses compared to clinically stable patients ($p=0.04$). FIG. 1F shows that RGC-32 mRNA expression levels were correlated with those of FasL in patients during relapses ($r=0.90$, $p<0.0001$).

FIG. 2A shows that EDSS was significantly higher in patients with relapses compared to clinically stable patients ($p=0.002$). FIG. 2B shows that EDSS was not significantly changed in responders vs. non-responders to GA treatment over two years.

FIG. 3A shows that significantly higher levels of RGC-32 mRNA were found in responders to glatiramer acetate compared to non-responders ($p<0.0001$).

FIG. 3B shows that significantly higher levels of FasL mRNA were found in responders to glatiramer acetate compared to non-responders ($p<0.0001$). FIGS. 3C-3D shows that levels of CDC2 and AKT mRNA were not significantly different between responders to glatiramer acetate and non-responders. FIG. 3E shows that significantly decreased levels of IL-21 mRNA were found in responders to glatiramer acetate compared to non-responders ($p=0.02$).

FIG. 4A shows that responders to glatiramer acetate showed persistently higher levels of RGC-32 compared to non-responders over time. FIG. 4B shows that a similar pattern was observed for FasL mRNA expression, with higher levels of mRNA expression seen in responders and lower levels in non-responders over time. FIG. 4C shows that responders to glatiramer acetate showed persistently lower levels of IL-21 compared to non-responders over time.

FIG. 6A shows that in the present cohort, a RGC-32/L13 ratio<1.27 is detected in patient relapse with a sensitivity of 71% and a specificity of 95%. FIG. 6B shows that a FasL/L13 ratio<52.6 is detected in a patient relapse with a sensitivity of 81% and a specificity of 95%. FIG. 6C shows that an IL-21/L13 ratio>16.9 is detected in a patient relapse with a sensitivity of 54% and a specificity of 88%.

FIG. 7A shows that in the present cohort, a RGC-32/L13 ratio>2.52 is detected in RRMS patient response to glatiramer acetate with a sensitivity of 71% and a specificity of 92%. FIG. 7B shows that a FasL/L13 ratio>85.4 is detected in a RRMS patient response to glatiramer acetate with a sensitivity of 85% and a specificity of 92%. FIG. 7C shows that an IL-21/L13 ratio<11.9 is detected in RRMS a patient response to glatiramer acetate with a sensitivity of 81% and a specificity of 89%.

FIGS. 9A-9B show that perivascular inflammatory cells were positive for RGC-32 at the arrows. FIG. 9C shows that RGC-32 (light gray deposits) was co-localized with CD3 (dark gray deposits) by double staining at the arrowheads in the parenchyma of an MS plaque; FIG. 9D is the control for the immunoperoxidase reaction.

DETAILED DESCRIPTION OF THE INVENTION

Figure 1A:
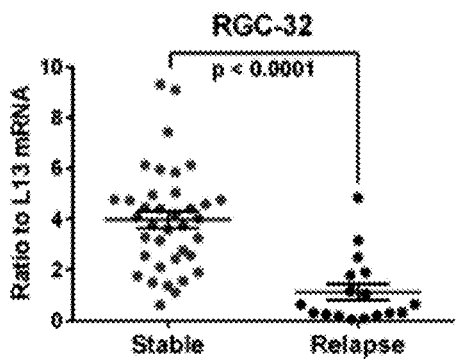
FIGS. 1A-1F show expression of RGC-32, FasL, CDC2, AKT, and IL-21 mRNA in stable MS patients and patients with acute relapses. Target gene mRNA expression was measured in patients' PBMCs using real-time qRT-PCR and expressed as a ratio to L13.

The following abbreviations may be used herein: AKT or AKT1-AKT8 virus oncogene cellular homolog; AUC-area under the curve; CDC2-cell division cycle protein 2 homolog; CNS-central nervous system; CPT-cell preparation tubes; EDSS-expanded disability status scale; FasL-fas ligand; GA-glatiramer acetate; IL-interleukin; MRI-magnetic resonance imaging; MS-multiple sclerosis; NRV-normalized mRNA value; PBMCs-peripheral blood mononuclear cells; RGC-response gene to complement; ROC-receiver operating characteristic; RRMS-relapsing-remitting multiple sclerosis; WT-wild type.

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "contacting" refers to any suitable method of bringing a compound or a composition into contact with a cell. For in vivo applications, any known method of administration is suitable as described herein.

As used herein, the term "subject" refers to any human or non-human recipient of the methods described herein or from whom a biological sample is obtained.

Generally, provided herein are methods utilizing normalized mRNA levels of Response Gene to Complement-32, FasL or IL-21 to determine the disease status of an individual with relapsing-remitting multiple sclerosis. Normalized mRNA levels are calculated from the ratio of a first mRNA level determined for Response Gene to Complement-32, FasL or IL-21 to a second mRNA level determined for L13. Comparison of normalized mRNA levels to cut-off levels for Response Gene to Complement-32, FasL or IL-21 is indicative of relapse or the stability of the multiple sclerosis and response to a treatment.

The present invention is directed to a method for determining whether an individual with relapsing-remitting multiple sclerosis will suffer a relapse, comprising the step of: measuring the mRNA level of Response Gene to Complement-32 in peripheral blood mononuclear cells of the individual; measuring the mRNA level of L13 in peripheral blood mononuclear cells of the individual; calculating a ratio of the mRNA levels of Response Gene to Complement-32 to the mRNA level of L13 to obtain a normalized level of Response Gene to Complement-32; and comparing the normalized level of Response Gene to Complement-32 to a cut-off value of 1.27, wherein a normalized level of Response Gene to Complement-32 less than 1.27 indicates that the individual will have or is having a relapse of multiple sclerosis.

A person having ordinary skill in this art would readily recognize that testing of levels of Response Gene to Complement-32 in an individual with relapsing-remitting multiple sclerosis can be undertaken in various time periods. For example, the levels of Response Gene to Complement-32 may be measured daily, weekly or monthly or any desired time periods.

In one preferred aspect of this method of the present invention, levels of said Response Gene to Complement-32 are measured on a daily basis. In this embodiment, a normalized level of Response Gene to Complement-32 less than 1.27 from one day to the next indicates that said individual will have or is having a relapse of multiple sclerosis.

In another preferred aspect of this method of the present invention, levels of said Response Gene to Complement-32 are measured on a weekly basis. In this embodiment, a normalized level of Response Gene to Complement-32 less than 1.27 from one week to the next indicates that said individual will have or is having a relapse of multiple sclerosis. In another preferred aspect of this method of the present invention, levels of said Response Gene to Complement-32 are measured on a monthly basis. In this embodiment, a normalized level of Response Gene to Complement-32 less than 1.27 from one month to the next indicates that said individual will have or is having a relapse of multiple sclerosis. As is well known, the levels of Response Gene to Complement-32 may be measured at the protein or mRNA level. For example, Response Gene to Complement-32 mRNA may measured by real time PCR or an oligonucleotide array. In one form, the Response Gene to Complement-32 mRNA is measured in peripheral blood mononuclear cells. In a non-limiting example, the peripheral blood mononuclear cells may be CD4$^+$ T-cells.

The present invention is further directed to a method for determining whether an individual with relapsing-remitting multiple sclerosis will suffer a relapse, comprising the step of: measuring the mRNA level of FasL in peripheral blood mononuclear cells of said individual; measuring the mRNA level of L13 in peripheral blood mononuclear cells of the individual; calculating a ratio of the mRNA levels of FasL to the mRNA level of L13 to obtain a normalized level of FasL; and comparing the normalized level of FasL to a cut-off value of 52.6, wherein a normalized level of FasL less than 52.6 indicates that the individual will have or is having a relapse of multiple sclerosis.

A person having ordinary skill in this art would readily recognize that testing of levels of FasL in an individual with relapsing-remitting multiple sclerosis can be undertaken in various time periods. For example, the levels of FasL may be measured daily, weekly or monthly or any desired time periods.

In one preferred aspect of this method of the present invention, levels of said FasL are measured on a daily basis. In this embodiment, a normalized level of FasL less than 52.6 from one day to the next indicates that said individual will have or is having a relapse of multiple sclerosis. In another preferred aspect of this method of the present invention, levels of said FasL are measured on a weekly basis. In this embodiment, a normalized level of FasL less than 52.6 from one week to the next indicates that said individual will have or is having a relapse of multiple sclerosis. In another preferred aspect of this method of the present invention, levels of said FasL are measured on a monthly basis. In this embodiment, a normalized level of FasL less than 52.6 from one month to the next indicates that said individual will have or is having a relapse of multiple sclerosis. As is well known, the levels of FasL may be measured at the protein or mRNA level. For example, FasL mRNA may measured by real time PCR or an oligonucleotide array. In one form, the FasL mRNA is measured in peripheral blood mononuclear cells. In a non-limiting example, the peripheral blood mononuclear cells may be CD4$^+$ T-cells.

The present invention is further directed to a method for determining whether an individual with relapsing-remitting multiple sclerosis will suffer a relapse, comprising the step of: measuring the mRNA level of IL-21 in peripheral blood mononuclear cells of the individual; measuring the mRNA level of L13 in peripheral blood mononuclear cells of the individual; calculating a ratio of the mRNA levels of IL-21 to the mRNA level of L13 to obtain a normalized level of IL-21; and comparing the normalized level of IL-21 to a cut-off value of 16.9, wherein a normalized level of IL-21 greater than 16.9 indicates that the individual will have or is having a relapse of multiple sclerosis.

A person having ordinary skill in this art would readily recognize that testing of levels of IL-21 in an individual with relapsing-remitting multiple sclerosis can be undertaken in various time periods. For example, the levels of IL-21 may be measured daily, weekly or monthly or any desired time periods.

In one preferred aspect of this method of the present invention, levels of said FasL are measured on a daily basis. In this embodiment, a normalized level of IL-21 greater than 16.9 from one day to the next indicates that said individual will have or is having a relapse of multiple sclerosis. In another preferred aspect of this method of the present invention, levels of said IL-21 are measured on a weekly basis. In this embodiment, a normalized level of IL-21 greater than 16.9 from one week to the next indicates that said individual will have or is having a relapse of multiple sclerosis. In another preferred aspect of this method of the present invention, levels of said IL-21 are measured on a monthly basis. In this embodiment, a normalized level of IL-21 greater than 16.9 from one month to the next indicates that said individual will have or is having a relapse of multiple sclerosis. As is well known, the levels of IL-21 may be measured at the protein or mRNA level. For example, IL-21 mRNA may measured by real time PCR or an oligonucleotide array. In one form, the IL-21 mRNA is measured in peripheral blood mononuclear cells. In a non-limiting example, the peripheral blood mononuclear cells may be $CD4^+$ T-cells.

The present invention is further directed to a method for determining whether an individual with relapsing-remitting multiple sclerosis will respond positively to glatiramer treatment for multiple sclerosis, comprising the step of: administering the glatiramer treatment to the individual; and measuring the mRNA levels of Response Gene to Complement-32, FasL and IL-21 in peripheral blood mononuclear cells of the individual after the treatment; measuring the mRNA level of L13 in peripheral blood mononuclear cells of the individual; calculating the mRNA levels of Response Gene to Complement-32, FasL and IL-21 by the mRNA level of L13 to obtain normalized levels of Response Gene to Complement-32, FasL and IL-21; and comparing the normalized levels of Response Gene to Complement-32, FasL and IL-21 to a cut-off values, wherein a normalized level of Response Gene to Complement-32 greater than 2.52, a normalized level of FasL greater than 85.4 and a normalized level of IL-21 less than 11.9, respectively in the individual indicates that the individual will respond positively or is responding positively to the treatment. Generally, mRNA levels of the Response Gene, FasL and IL-21 to Complement-32 may be measured daily, weekly or monthly.

For example, a normalized level of Response Gene to Complement-32 greater than 2.52, a normalized level of FasL greater than 85.4 and/or a normalized level of IL-21 less than 11.9, in the individual from one measurement to the next, such as one or more days, one or more weeks or one or more months, indicates that the individual will respond positively or is responding positively to glatiramer treatment. Preferably, the peripheral blood mononuclear cells are $CD4^+$ T-cells.

The present invention is further directed to a method for determining whether an individual with relapsing-remitting multiple sclerosis is in a period of stable disease or is not at risk for relapse of multiple sclerosis, comprising the steps of: measuring mRNA level of Response Gene to Complement-32, FasL and IL-21 in peripheral blood mononuclear cells of the individual for at least two times sequentially; measuring the mRNA level of L13 in peripheral blood mononuclear cells of the individual; calculating the mRNA levels of Response Gene to Complement-32 by the mRNA level of L13 to obtain a normalized level of Response Gene to Complement-32; and comparing the normalized level of Response Gene to Complement-32 to a previous measurement of normalized level of Response Gene to Complement-32, wherein a significantly higher normalized level of Response Gene to Complement-32 than a previous measurement thereof in the individual indicates that the individual is in a period of stable disease or is not at risk for relapse of multiple sclerosis. Within the context of the methods of the present invention, the term "significantly" refers to a statistically significant difference from one measurement to the next. Thus, a "significant" reduction or increase is one that reaches statistical relevance or significance. The mRNA level may be measured by real time PCR or an oligonucleotide array.

The following example(s) are given for the purpose of illustrating various embodiments of the invention and are not meant to limit the present invention in any fashion.

EXAMPLE 1

Materials and Methods
Patients and Controls

A total of 15 patients with RRMS were enrolled. The patients were recruited from the University of Maryland Multiple Sclerosis Center. The mean age was 40 (range, 22-60), and consisted of 60% females (n=9) and 40% males (n=6). The criteria for inclusion of multiple sclerosis patients in the study were: (i) age 18 to 65 years; (ii) fulfillment of the McDonald criteria for definite multiple sclerosis (13-14); (iii) relapsing-remitting course; (iv) having newly diagnosed multiple sclerosis, or multiple sclerosis not treated with currently used immunomodulatory drugs (interferon-β or glatiramer acetate) for 3 months prior to study entry; (v) no exacerbations in the 4 weeks before the study; (vi) no i.v. or p.o. steroids for 4 weeks prior to study enrollment; (vii) no treatment with Tysabri, Gilenya, mitoxantrone, cyclophosphamide, or any investigational drug during the past year; and (viii) a disability score of 0-5.5, as defined by the expanded disability status scale (EDSS) (15). Exclusion criteria for multiple sclerosis patients were: (i) a history of autoimmune disorders, vascular disease, or active acute or chronic infections; (ii) use of antibiotics in the last 30 days; (iii) a history of intracranial or intraspinal tumor or metabolic myelopathy; or (iv) a history of alcohol or drug abuse.

All multiple sclerosis patients received 20 mg of glatiramer acetate (GA) injected subcutaneously every day for 2 years. During this period of 2 years, patients were clinically evaluated and peripheral blood samples were collected at 0, 3, 6, and 12 months at the time of their outpatient visits. Patients with symptoms suggestive of a clinical relapse called the University of Maryland Multiple Sclerosis Center. Clinical relapse was defined as substantial worsening of pre-existing symptoms or appearance of new neurological deficits in the absence of fever or infections lasting more than 24 h. An EDSS evaluation was completed at each visit. Clinical records, consultation reports, and inpatient records were reviewed by a neurologist to ensure that the data obtained were complete. In the case of patients with relapse, the administration of 1g of Solu-Medrol i.v. for 3 days was used to treat the disease exacerbation. A prednisone taper was also used after i.v. Solu-Medrol in certain cases. In such cases, blood samples were obtained prior to Solu-Medrol treatment. Responders to glatiramer acetate treatment were defined as patients who exhibited 0 or no more than 1 relapse event during the 2 year span following the initiation of glatiramer acetate. Non-responders were defined as patients who exhibited 2 or more relapse events during the 2 year span following the initiation of glatiramer acetate. According to these criteria, the present cohort consisted of 11 responders (mean age 43, range 27-60; 55% female) and 4 non-responders (mean age 31, range 22-36; 75% female).

Collection of PBMCs, Total RNA Purification, and cDNA Synthesis

PBMCs were collected using BD Vacutainer CPT tubes (Becton Dickinson, Franklin Lakes, N.J.). The mononuclear cells were isolated from fresh blood as previously described (11). RNA isolation was performed the same day, as previously described (12). Total RNA was purified using an RNeasy Mini Kit (Qiagen, Santa Clarita, Calif.) according to the manufacturer's instructions. RNA (0.5 μg per sample) was mixed with RT buffer, dNTP, and oligo-dT random primers (Invitrogen). RNA was denatured by incubation at 65° C. for 5 min. The reverse transcriptase (Promega) and RNase inhibitor (Invitrogen) were then added, and the reaction mixture was incubated at 37° C. for 1 h to synthesize cDNA. The reaction was terminated by incubating the mixture at 95° C. for 5 min.

Real-time Quantitative PCR

Real-time PCR was performed using a StepOne real-time PCR system (Applied Biosystems, Foster City, Calif.). The primers for the genes investigated were designed and synthesized by IDT (Coralville, Iowa) (Table I) and used in conjunction with LightCycler FastStart DNA Master SYBR Green I (Roche) along with sample cDNA according to the manufacturer's protocol. As a negative control for each real-time PCR assay, the same reaction was performed in the absence of cDNA. For each gene, the cycle threshold ($C_T$) values were determined in the exponential phase of the amplification plot and normalized to the mRNA expression of L13 ribosomal protein, a housekeeping gene. A standard curve was generated using serial dilutions of qPCR Human Reference Total cDNA (Clontech, Mountain View, Calif.), and the normalized mRNA value (NRV) was calculated according to the following formula for relative expression of target mRNA: NRV=(TarS/L13), where TarS represents the level of mRNA expression of the target gene, and L13 corresponds to that of the amplified L13 mRNA (11).

TABLE 1

| Gene Symbol | Sequence | Product (base pairs) |
|---|---|---|
| RCG-32 | Forward: 5'-AGGAACAGCTTCAGCTTCAG-3' (SEQ ID NO: 1) Reverse: 5'-GCTAAAGTTTTGTCAAGATCAGCA-3' (SEQ ID NO: 2) | 152 |
| FasL | Forward: 5'-GCCCATTTAACAGGCAAGTC-3' (SEQ ID NO: 3) Reverse: 5'-ATCACAAGGCCACCCTTCTT-3' (SEQ ID NO: 4) | 110 |
| CDC2 | Forward: 5'-TTTTCAGAGCTTTGGGCACT-3' (SEQ ID NO: 5) Reverse: 5'-AGGCTTCCTGGTTTCCATTT-3' (SEQ ID NO: 6) | 100 |
| L13 | Forward: 5'-CGTGCGTCTGAAGCCTACA-3' (SEQ ID NO: 7) Reverse: 5'-GGAGTCCGTGGGTCTTGAG-3' (SEQ ID NO: 8) | 227 |

TABLE 1-continued

| Gene Symbol | Sequence | Product (base pairs) |
|---|---|---|
| AKT1 | Forward: 5'-ACGCCAAGGAGATCATGC-3' (SEQ ID NO: 9) Reverse: 5'-CTCCATGCTGTCATCTTGGTC-3' (SEQ ID NO: 10) | 185 |

RGC-32, Response gene to complement 32;
FasL, Fas ligand;
CDC2, cell division control protein 2,
L13, ribosomal protein L13.
IL-21 primers were purchased from SABiosciences, cat# PPH01684A Statistical Analysis Comparisons between groups were performed using a two-tailed t-test assuming unequal variances. P values<0.05 were considered significant. Pearson correlation analysis was conducted to examine the association between variables. Statistical analysis was performed using IBM SPSS Statistics software version 22 and GraphPad Prism software version 6. All values are shown as mean±SEM and are representative of three experiments unless otherwise noted. Receiver operating characteristic (ROC) curve analysis was used to assess the predictive accuracy of each potential biomarker. The predictive probability of binary outcomes regarding clinical state and response to glatiramer acetate treatment was reported as a C-statistic or Area Under the Curve (AUC, represented as a percentage, with a perfect score being 100% predictability).

EXAMPLE 2

Expression of RGC-32, FasL, CDC2, AKT, and IL-21 mRNA in Acute MS Relapse

Figure 1B:
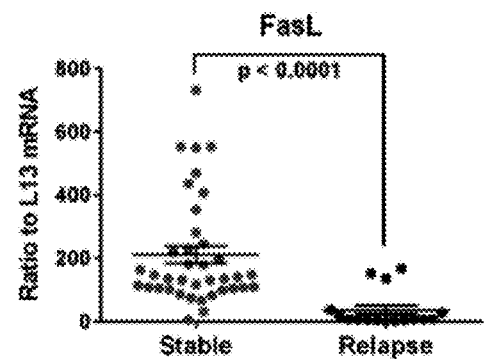
Figure 1C:
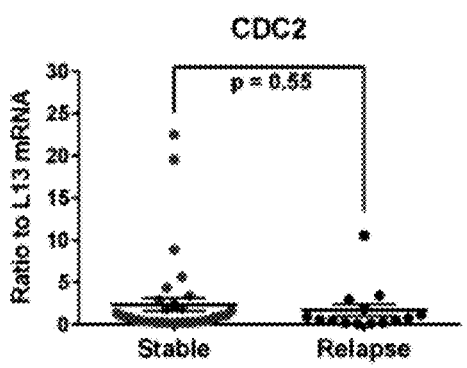
Figure 1D:
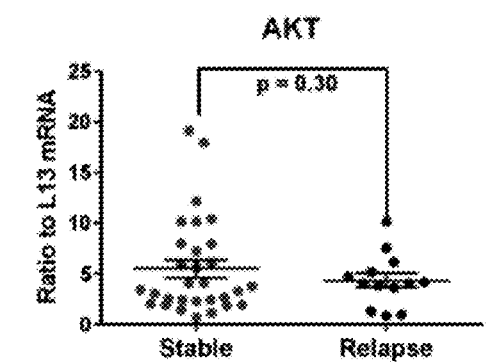
Figure 1E:
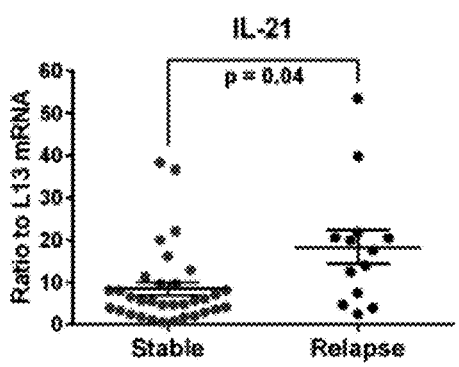
Figure 1F:
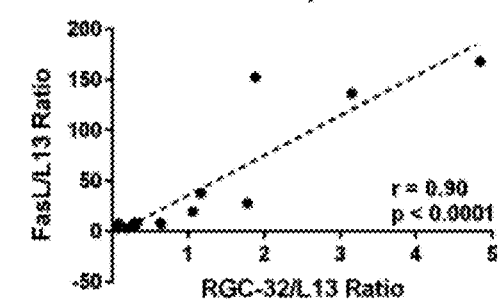
Figure 2A:
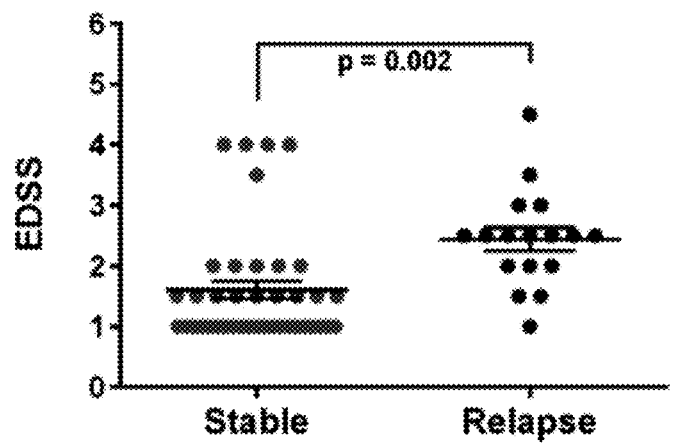
FIGS. 2A-2B show the expanded disability status scale (EDSS) of MS patients by clinical state and response to glatiramer acetate. EDSS was determined as described below.
Figure 2B:
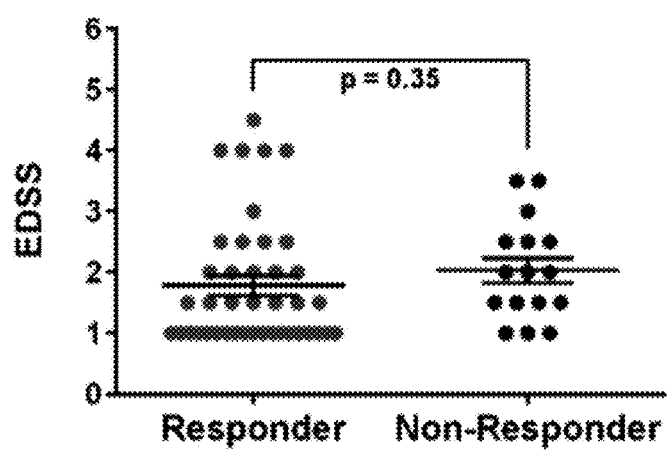

The expression of RGC-32 mRNA in unstimulated PBMCs in relation to disease activity was first examined. FasL and CDC2 mRNA expression were also investigated. In addition, IL-21 and AKT mRNA expression were investigated. Multiple sclerosis patient PBMC samples were categorized into those from stable periods in which no clinical activity was present and those from periods of relapse, in which clinical activity was present and had been detected by a neurologist. Target gene mRNA expression was measured in patients' PBMCs using real-time qRT-PCR and expressed as a ratio to L13. Statistically significant lower levels of RGC-32 mRNA were found in multiple sclerosis patients with relapses compared to those who were clinically stable (p<0.0001) (FIG. 1A). Patients with relapses also exhibited significantly lower levels of FasL mRNA compared to stable multiple sclerosis patients (p<0.0001) (FIG. 1B). Levels of CDC2 and AKT mRNA in multiple sclerosis patients with relapses were similar to those in stable patients (FIGS. 1C-1D). On the other hand, IL-21 mRNA expression was significantly higher in multiple sclerosis patients with relapses compared to stable multiple sclerosis patients (p=0.04) (FIG. 1E). As shown in FIG. 1F, RGC-32 and FasL mRNA expression levels were positively correlated within multiple sclerosis patients during relapses (r=0.90, p<0.0001). Furthermore, the mean EDSS score was significantly higher in patients with relapses compared to stable patients (p=0.002) (FIG. 2A). However, the mean EDSS score was not significantly different between glatiramer acetate responders and non-responders overall (p=0.35) (FIG. 2B).

EXAMPLE 3

Figure 3A:
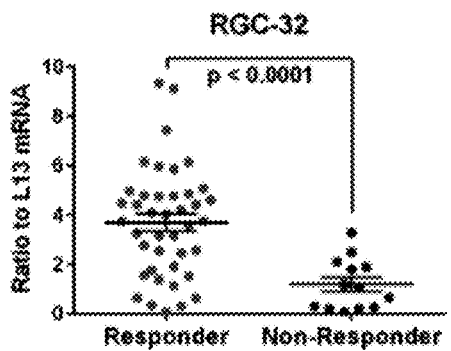
FIGS. 3A-3E shows expression of RGC-32, FasL, CDC2, AKT, and IL-21 mRNA in responders and non-responders to glatiramer acetate treatment. Target gene mRNA expression was measured in patients' PBMCs using real-time qRT-PCR and expressed as a ratio to L13.
Figure 3B:
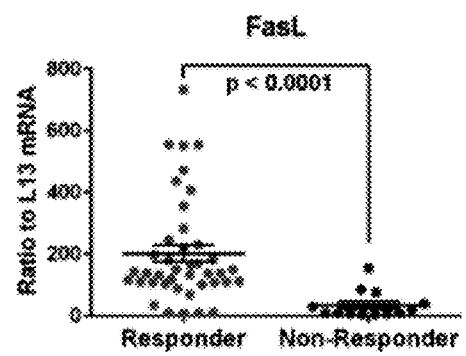
Figure 3C:
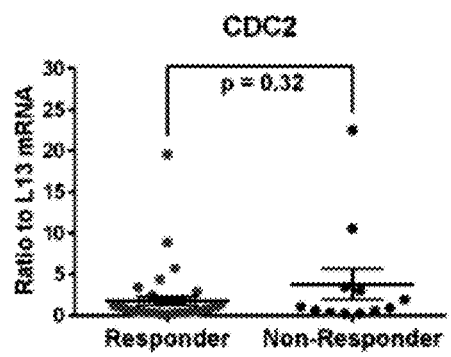
Figure 3D:
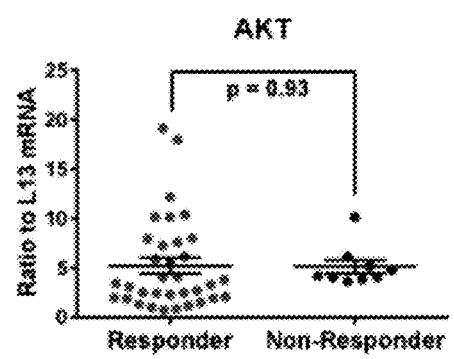
Figure 3E:
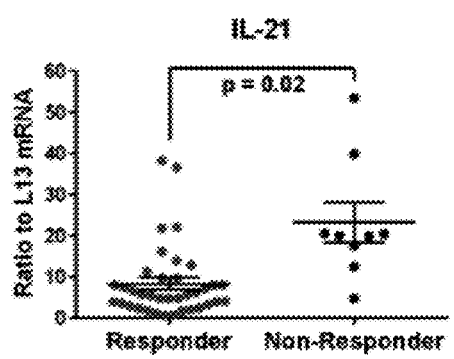

Expression of RGC-32, FasL, CDC2, AKT, and IL-21 mRNA in Responders vs. Non-Responders to GA Treatment Since glatiramer acetate is an effective treatment for RRMS, the relationship between RGC-32, FasL, CDC2, AKT, and IL-21 mRNA expression and responsiveness to treatment over time was examined. Responders to glatiramer acetate treatment were defined as patients who exhibited 0 or no more than 1 relapse event during the 2 year span following the initiation of glatiramer acetate whereas non-responders exhibited 2 or more relapse events. Overall, responders to glatiramer acetate treatment showed significantly higher levels of RGC-32 ($p<0.0001$) and FasL ($p<0.0001$) (FIGS. 3A-3B). No significant change was observed in CDC2 or AKT expression between responders and non-responders (FIGS. 3C-3D). IL-21 mRNA levels were lower in responders to glatiramer acetate treatment compared to non-responders ($p=0.02$) (FIG. 3E).

Figure 4A:
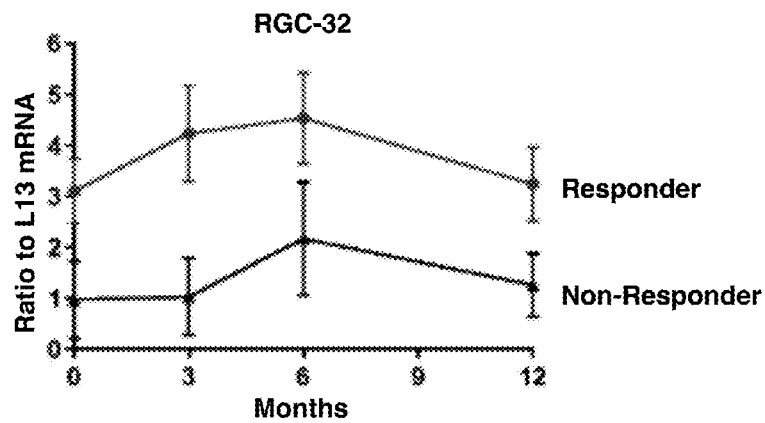
FIGS. 4A-4C show the time course of RGC-32, FasL, and IL-21 mRNA expression in glatiramer acetate-treated MS patients. PBMCs were obtained from patients with RRMS at 0, 3, 6, and 12 months following the initiation of glatiramer acetate treatment. Target gene mRNA expression was measured in patients' PBMCs using real-time qRT-PCR and expressed as a ratio to L13.
Figure 4B:
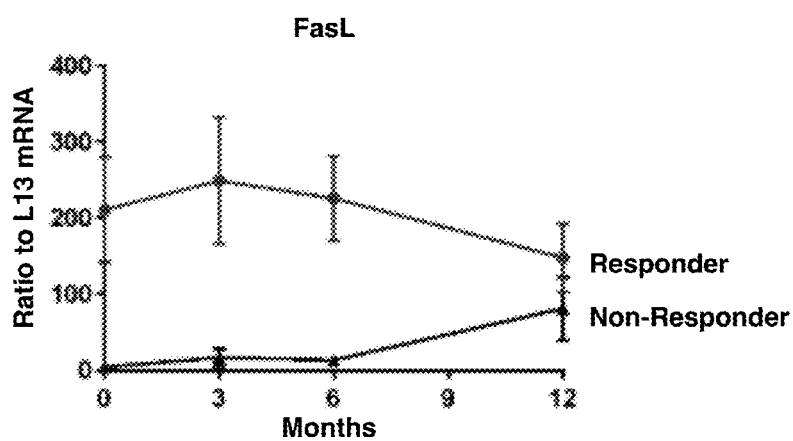
Figure 4C:
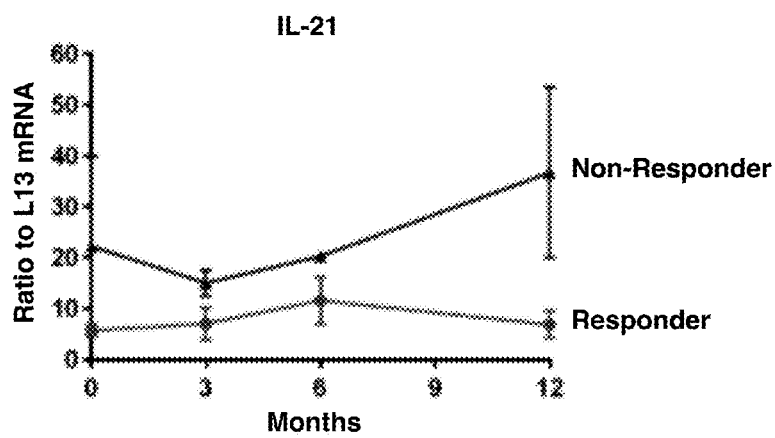

Over time, responders to glatiramer acetate showed persistently higher levels of RGC-32, whereas non-responders showed persistently lower levels (FIG. 4A). A similar pattern was observed for FasL (FIG. 4B), with higher levels of mRNA expression seen in responders and lower levels seen in non-responders over time. Conversely, over time responders to glatiramer acetate showed persistently lower levels of IL-21, whereas non-responders showed persistently higher levels (FIG. 4C). CDC2 and AKT mRNA expression did not exhibit a pattern that differed between responders and non-responders over time (data not shown).

Figure 5A:
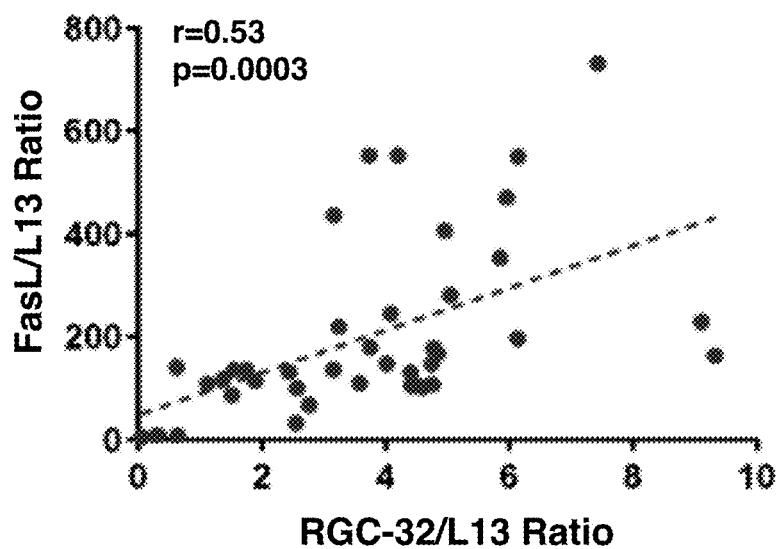
FIGS. 5A-5B show correlation of RGC-32 and FasL mRNA in glatiramer acetate-treated MS patients. RGC-32 mRNA levels were correlated with those of FasL in both responders (FIG. 5A) and non-responders during relapses (FIG. 5B). The Pearson correlation coefficient for responders was $r=0.53$ ($p=0.0003$), and $r=0.74$ ($p=0.01$) for non-responders.
Figure 5B:
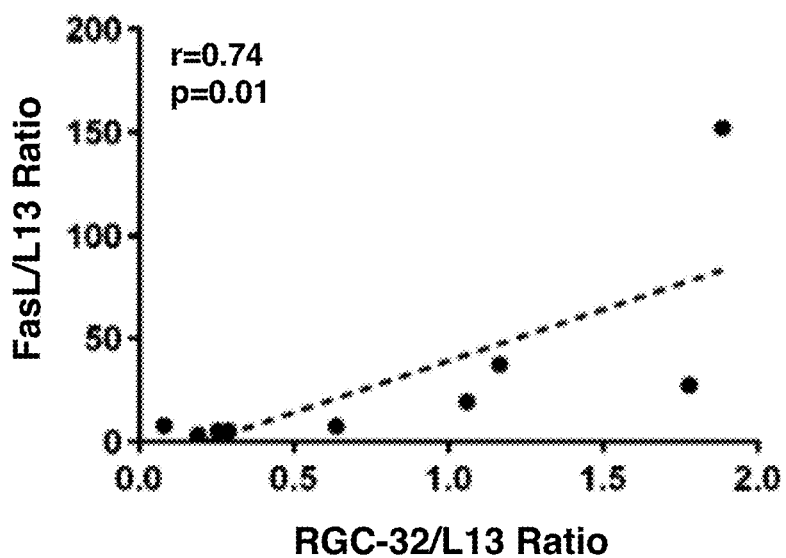

Furthermore, RGC-32 and FasL mRNA levels were positively correlated within responders during periods of both remission and relapse, as well as non-responders during relapse (FIGS. 5A-5B). Pearson correlation coefficients were $r=0.53$ ($p=0.0003$) for responders and $r=0.74$ ($p=0.01$) for non-responders during relapse. No statistically significant correlations were found between EDSS scores and any of the target genes examined (data not shown).

EXAMPLE 4

ROC Analysis

Figure 6A:
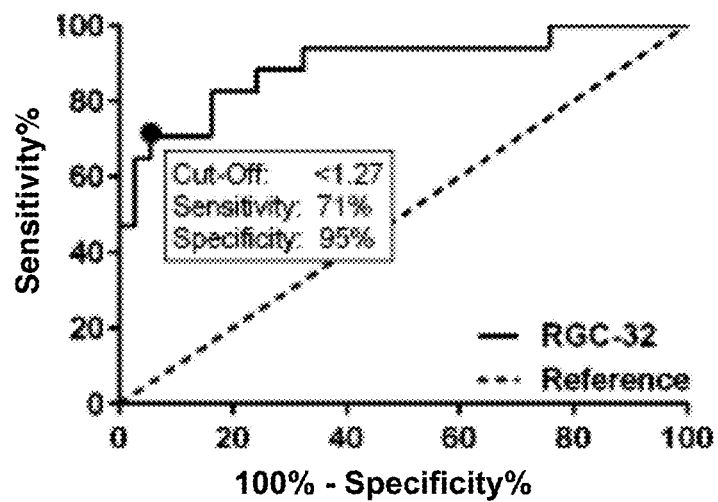
FIGS. 6A-6C show ROC curve analysis to assess the predictive accuracy of RGC-32, FasL, and IL-21 in detecting MS patient relapse. The probability (C-statistic, or AUC) of accurately detecting relapse was 90% using RGC-32 ($p<0.0001$), 88% using FasL ($p<0.0001$), and 75% using IL-21 ($p=0.01$).
Figure 6B:
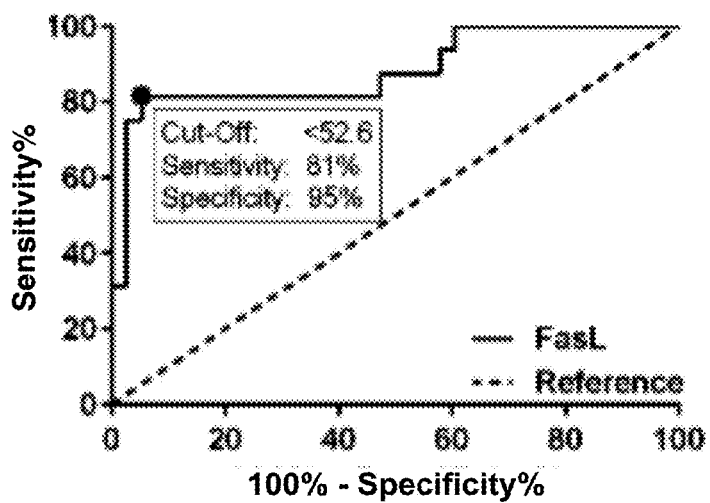
Figure 6C:
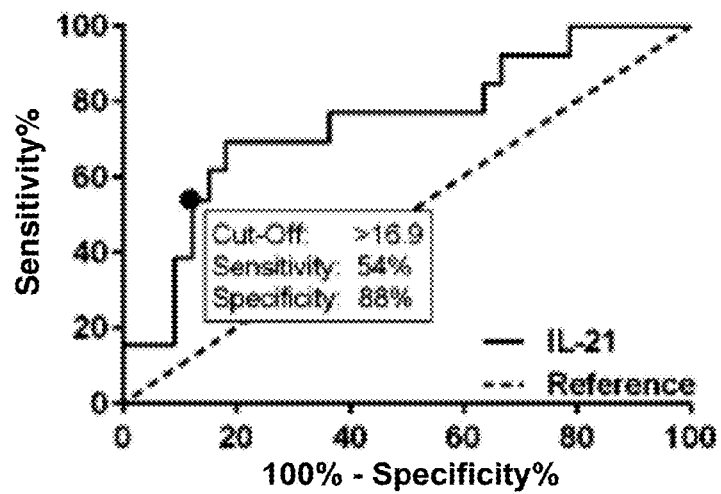

ROC analysis was used to assess the predictive accuracy of using mRNA levels of each putative biomarker to detect patient relapse. The probability (C-statistic, or AUC) of accurately detecting relapse was 90% using RGC-32 (95% CI 80-99%, $p<0.0001$), 88% using FasL (95% CI 77-99%, $p<0.0001$), and 75% using IL-21 (95% CI 58-91%, $p=0.01$) (FIGS. 6A-6B). In the present cohort, a RGC-32/L13 ratio<1.27 detected patient relapse with a sensitivity of 71% (95% CI 44-90%) and a specificity of 95% (95% CI 82-99%) (FIG. 6A). A FasL/L13 ratio<52.6 detected patient relapse with a sensitivity of 81% (95% CI 54-96%) and a specificity of 95% (95% CI 82-99%) (FIG. 6B). An IL-21/L13 ratio>16.9 detected patient relapse with a sensitivity of 54% (95% CI 25-81%) and a specificity of 88% (95% CI 72-97) (FIG. 6C).

Figure 7A:
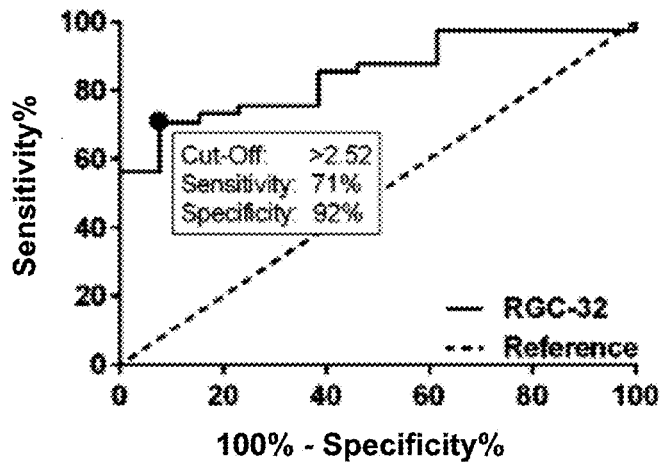
FIGS. 7A-7C show ROC curve analysis to assess the predictive accuracy of RGC-32, FasL, and IL-21 in detecting MS patient response to glatiramer acetate. The probability (C-statistic, or AUC) of accurately detecting response to glatiramer acetate treatment over 2 years was 85% using RGC-32 ($p=0.0002$), 90% using FasL ($p<0.0001$), and 85% using IL-21 ($p=0.001$).
Figure 7B:
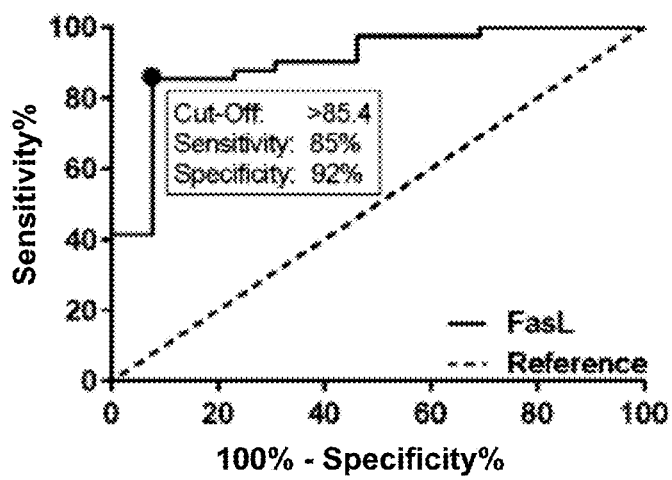
Figure 7C:
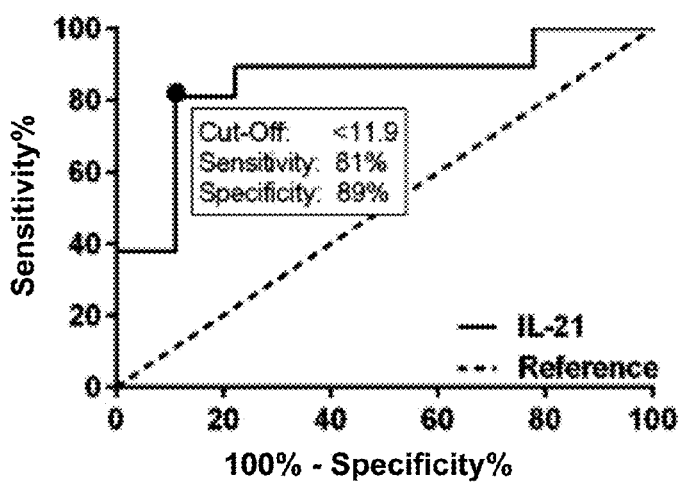

Since persistently higher levels of RGC-32 and FasL as well as lower levels of IL-21 mRNA were associated with a good response to glatiramer acetate treatment over time, ROC analysis was also used to assess the predictive accuracy of RGC-32, FasL, and IL-21 in detecting response to glatiramer acetate. The probability (C-statistic, or AUC) of accurately detecting response to glatiramer acetate treatment over 2 years was 85% using RGC-32 (95% CI 74-95%, $p=0.0002$), 90% using FasL (95% CI 81-100%, $p<0.0001$), and 85% using IL-21 (95% CI 71-99%, $p=0.001$) (FIGS. 7A-7C). In the present cohort, a RGC-32/L13 ratio>2.52 correctly detected patient response to glatiramer acetate with a sensitivity of 71% (95% CI 54-84%) and a specificity of 92% (95% CI 64-100%). A FasL/L13 ratio>85.4 correctly detected patient response to glatiramer acetate with a sensitivity of 85% (95% CI 71-94%) and a specificity of 92% (95% CI 64-100%). An IL-21/L13 ratio<11.9 correctly detected patient response to glatiramer acetate with a sensitivity of 81% (95% CI 65-92%) and a specificity of 89% (95% CI 52-100%).

Additionally, ROC curve analysis was performed using only baseline mRNA levels from samples collected prior to glatiramer acetate administration (i.e. at month 0) to assess the predictive accuracy of initial RGC-32, FasL, and IL-21 levels in predicting future response to glatiramer acetate. The probability (C-statistic, or AUC) of accurately predicting response to glatiramer acetate was 82% using RGC-32 (95% CI 58-100%, $p=0.10$), 100% using FasL (95% CI 100-100%, $p=0.03$), and 75% using IL-21 (95% CI 35-100%, $p=0.28$) (data not shown).

EXAMPLE 5

RGC-32 Regulation of IL-21 Expression

Figure 8:
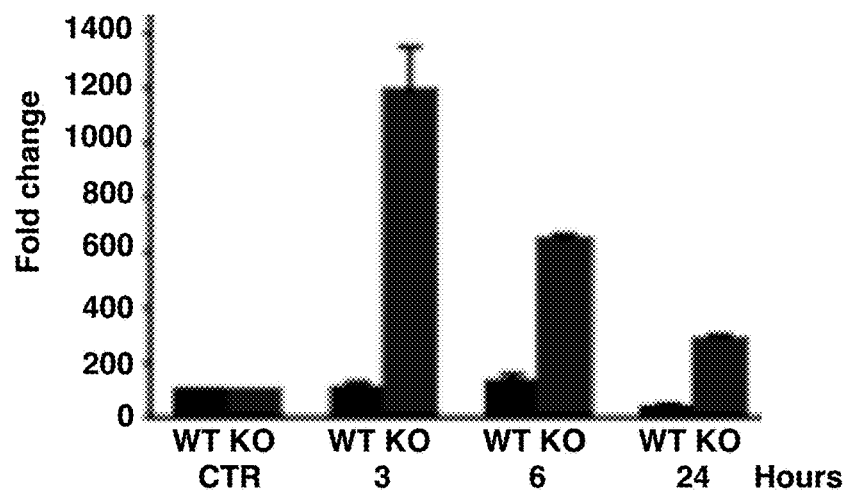
FIG. 8 shows RGC-32 regulates IL-21 mRNA expression. Purified CD4$^+$ T cells from wild-type (WT) or RGC-32–/– knockout (KO) mice were stimulated with anti-CD3 (5 µg/mL) and soluble anti-CD28 (2.5 µg/mL) for the indicated periods of time. IL-21 mRNA expression was significantly increased after 3, 6 and 24 h of stimulation ($p<0.001$) in RGC-32–/– mice. Results of three separate experiments are expressed as mean±SEM.

IL-21 is involved with T-cell proliferation and cell cycle activation. In FIG. 8 CD4$^+$ T-cells from RGC-32 knockout mice showed increased expression of IL-21 mRNA in the absence of RGC-32 in CD4$^+$ T-cells stimulated with anti-CD3/CD28. This suggests an inhibitory effect of RGC-32 on IL-21 transcription, which may explain the inverse relationship between RGC-32 and IL-21 mRNA levels as observed.

EXAMPLE 6

Expression of RGC-32 in Multiple Sclerotic Brain

Using indirect immunoperoxidase staining, the present invention shows that RGC-32 is expressed in both acute and chronic active lesions. The RGC-32 deposition extended from the MS plaques to normal adjacent white and gray matter lesions (FIGS. 2A-2D). By using double-staining immunohistochemistry, it was demonstrated that some of CD3$^+$ cells in MS plaques co-localized with RGC-32. The RGC-32 also co-localized with CD68$^+$ macrophages (10-11).

The expression of RGC-32 mRNA was measured in MS patients and controls by real time PCR and expressed as ratio L13. A statistically significant decrease of RGC-32 was found in patients with relapses when compared with stable MS patients and controls. RGC-32 levels were found to be significantly higher in stable MS patients. controls. RGC-32 levels were found to be significantly higher in stable MS patients.

Figure 9A:
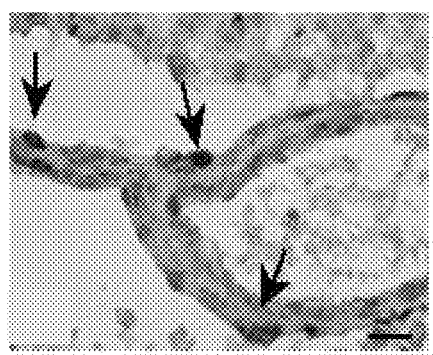
FIGS. 9A-9D show the expression of RGC-32 on inflammatory cells in MS brain. MS plaques cryostat sections were immunostained by the ABC method using an rabbit IgG anti-RGC-32.
Figure 9B:
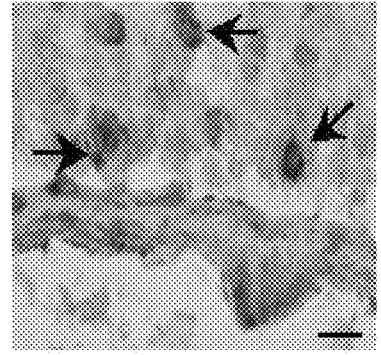
Figure 9C:
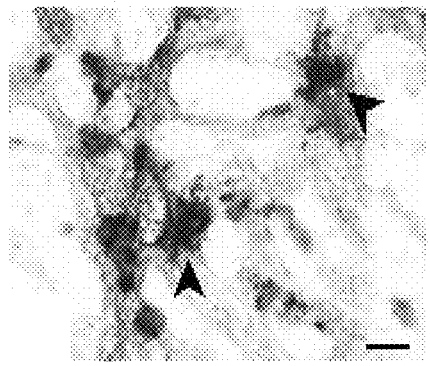
Figure 9D:
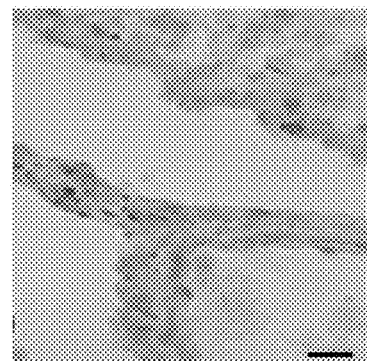

FIGS. 9A-9B shows the expression of RGC-32 on inflammatory cells in MS brain. MS plaques cryostat sections were immunostained by the ABC method using an rabbit IgG anti-RGC-32. FIGS. 9A-9B show that perivascular inflammatory cells were positive for RGC-32 compared to control (FIG. 9D). In FIG. 9C RGC-32 (light gray deposits) were co-localized with CD3 (dark grey deposits) by double staining at the arrowheads in the parenchyma of an MS plaque compared to control for the immunoperoxidase reaction.

TABLE 2

| Case | Sex | Age | Lesion types | No. of lesions | Lesional activity | Perivascular infiltrate | Parenchymal infiltrate/ microglia |
|---|---|---|---|---|---|---|---|
| 1 | F | 47 | Frontal plaque | 3 | Chronic active | +++ | + |
|   |   |   |   |   | NLWM | ++ | ++ |
|   |   |   |   |   | NLGM | + | ++ |
| 2 | M | 50 | Frontal plaque | 1 | NLGM | +++ | − |
| 3 | M | 50 | Temporal Plaque | 3 | Acute | ++ | +++ |
|   |   |   |   |   | NLWM | ++ | ++ |
|   |   |   |   |   | NLGM | + | + |
| 4 | M | 50 | Occipital Plague | 1 | NLWM | +/++ | +++ |
| 5 | F | 51 | Frontal plaque | 3 | Acute | ++ | ++ |
|   |   |   |   |   | NLWM | ++ | +++ |
|   |   |   |   |   | NLGM | ++ | ++ |
| 6 | F | 51 | Occipital Plaque | 3 | Chronic active | +++ | +++ |
|   |   |   |   |   | NLWM | +++ | +++ |
|   |   |   |   |   | NLGM | ++ | + |
| 7 | F | 38 | Parietal plaque | 3 | Chronic active | ++ | ++ |
|   |   |   |   |   | NL MW | + | ++ |
|   |   |   |   |   | NL GW | + | + |
| 8 | F | 38 | Occipital Plaque | 3 | Chronic active | +++ | +++ |
|   |   |   |   |   | NLWM | +++ | +++ |
|   |   |   |   |   | NLGM | ++ | ++ |

NLAM: non-lesional white matter,
NLGM: non-lesional gray matter,

As shown in the Table 2 above, the present invention demonstrates that inflammatory cells expressing RGC-32 cross the brain blood barrier during acute events and infiltrate multiple sclerosis lesions in patients with acute and chronic active multiple sclerosis. This data also supports the hypothesis that the changes in RGC-32 mRNA that are related to clinical activity are a result of the migration of inflammatory cells to the central nervous system.

The present invention shows that RGC-32 can serve as a biomarker for relapse in multiple sclerosis (MS) patients and that administration of glatiramer acetate, is associated with alterations in RGC-32 expression. Specifically, there are correlations between the level of RGC-32 and the response of MS patients to treatment. The present invention establishes a role for RGC-32 in multiple sclerosis as a possible biomarker of relapses and as a predictor of response to treatment. By measuring the level of RGC-32 expression in PBMCs, a person having ordinary skill in this art could use such analyses as a test for predicting relapses and response to multiple sclerosis drugs, such as glatiramer acetate (Copaxone) therapy in clinical practice.

Discussion

The present invention demonstrates the use of RGC-32, FasL, and IL-21 as biomarkers of relapse and response to glatiramer acetate treatment in a cohort of multiple sclerosis patients over time. This analysis was performed in unstimulated PBMCs in order to mimic the in vivo situation as closely as possible, so that alterations in mRNA expression would have greater predictive value with respect to clinical exacerbations.

The present invention demonstrates that RGC-32 and FasL mRNA levels are significantly decreased and IL-21 levels are increased in the PBMCs of multiple sclerosis patients during clinical relapse compared to remission. Furthermore, ROC analysis of this cohort showed that RGC-32, FasL, and IL-21 mRNA levels accurately detected patient relapse. Together, these findings support the use of RGC-32, FasL, and IL-21 as serum biomarkers of disease activity in multiple sclerosis.

Overall, RGC-32 and FasL mRNA levels were significantly increased and IL-21 levels were decreased in the PBMCs of multiple sclerosis patients defined as responders compared to non-responders to glatiramer acetate. Over time, RGC-32 and FasL levels were persistently higher and IL-21 levels were persistently lower in responders versus non-responders as well. Furthermore, ROC analysis of this cohort showed that RGC-32, FasL, and IL-21 mRNA levels accurately detected patient response to glatiramer acetate. Together, these findings show that RGC-32, FasL, and IL-21 are serum biomarkers of response to glatiramer acetate in multiple sclerosis. While these data support the use of RGC-32, FasL, and IL-21 mRNA levels within PBMCs to aid in the detection of response while using glatiramer acetate, these values can also be used to predict future response solely according to the baseline levels of RGC-32, FasL, and IL-21 recorded prior to glatiramer acetate initiation.

Although RGC-32 has been shown to bind with and modulate the activities of both CDC2 and AKT within the cell cycle, it appears as though changes in RGC-32 mRNA expression do not correlate with those of CDC2 and AKT during multiple sclerosis relapse or with respect to glatiramer acetate response. However, it is possible that differences exist at the levels of protein expression and function.

The synchronized changes observed in RGC-32 and FasL mRNA expression within PBMCs either during relapses or with respect to glatiramer acetate therapy response may be explained by the known role of RGC-32 in the regulation of FasL expression. Since RGC-32 binds to and up-regulates CDC2/cyclin B1 kinase activity, FasL expression in T-cells is regulated in part by the CDC2/cyclin B1 complex, and RGC-32 silencing significantly decreases FasL mRNA expression, it is possible that RGC-32 regulates FasL expression by modulating the activity of the CDC2/cyclin B1 complex. These data also suggest that RGC-32 is involved in regulating T-cell apoptosis by modulating the expression of FasL. In multiple sclerosis, myelin and myelin-producing oligodendrocytes in the CNS are targeted for autoimmune attack via antigen-specific CD4+ T cells. T-cell apoptosis in multiple sclerosis is regulated in part by the Fas-FasL system, and ex-vivo studies have demonstrated an increased resistance of T-cells to Fas-mediated apoptosis during multiple sclerosis relapses. Thus, in this case a decrease in RGC-32 and an associated decrease in FasL expression may result in a decrease in FasL-mediated T-cell apoptosis, promote the survival of myelin-targeted T-cells, and result in the onset of clinical relapse and a suboptimal response to glatiramer acetate treatment.

Overall, the data suggest that RGC-32, FasL and IL-21 serve as serum biomarkers for the detection of multiple sclerosis patient relapse and response to GA therapy. Such information is useful to help guide treatment decisions, delay disease progression, and improve outcomes for multiple sclerosis patients. Furthermore, RGC-32, FasL and IL-21 represent useful new targets for therapeutic intervention in multiple sclerosis.

The following references were cited herein:
1. Badea et al. 1998. *J Biol Chem,* 273:26977-26981 (1998)
2. Badea et al. *J Biol Chem,* 277:502-508 (2002).
3. Fosbrink et al. *Exp Mol Pathol,* 86:87-94 (2009).
4. Zipp et al. *J Neuroimmunol,* 86:151-154 (1998).
5. Sharief, M. K., *J Neuroimmunol,* 109:236-243 (2000).
6. Aktas et al. *Neuroscientist,* 12:305-316 (2006).
7. Okuda et al. *J Neuroimmunol,* 171:163-170 (2006).
8. Lopatinskaya et al. *J Neuroimmunol,* 138:123-131 (2003).
9. Torgler et al. *J Biol Chem,* 279:37334-37342 (2004).
10. Tegla et al. *Multiple Sclerosis,* 15:S189 (2009).
11. Tegla et al. *Exp. Mol. Pathol.,* 94:17-28 (2013).
12. Niculescu et al. *J Immunol,* 158:4405-4412 (1997).
13. McDonald, et al. *Ann Neurol,* 50:121-127 (2001).
14. Polman et al. *Ann Neurol,* 58:840-846 (2005).
15. Kurtzke, J. F. *Neurology,* 33:1444-1452 (1983).
16. Rus et al. *P Natl Acad Sci USA,* 102:11094-11099 (2005).

One skilled in the art will appreciate that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

What is claimed is:

1. A method for treating an individual with relapsing-remitting multiple sclerosis that is at risk for a relapse comprising the steps of:
   a) collecting a peripheral blood sample from the individual;
   b) isolating peripheral blood mononuclear cells from said peripheral blood sample;
   c) measuring Response Gene to Complement-32 mRNA in said peripheral blood mononuclear cells;
   d) measuring L13 mRNA in said peripheral blood mononuclear cells;
   e) diagnosing the individual as being at risk for a relapse based on a ratio of measured Response Gene to Complement-32 mRNA to the L13 mRNA of 1.27 or less; and
   f) administering a multiple sclerosis treating drug to the individual diagnosed as being at risk of relapse.

2. The method of claim 1, further comprising repeating the steps a) to d) on the individual daily, weekly or monthly.

3. The method of claim 1, further comprising:
   measuring at least one of FasL mRNA or IL-21 mRNA in the peripheral blood mononuclear cells;
   diagnosing the individual as being at risk for relapse based on a ratio of at least one of the measured FasL mRNA to L13 mRNA of 52.6 or less or the measured IL-21 mRNA to L13 mRNA of 16.9 or greater.

4. The method of claim 1, wherein the multiple sclerosis treating drug is glatiramer acetate or interferon-β.

5. A method for treating an individual with relapsing-remitting multiple sclerosis that is at risk for a relapse comprising the steps of:
   a) collecting a peripheral blood sample from the individual;
   b) isolating peripheral blood mononuclear cells from said peripheral blood sample;
   c) measuring FasL mRNA in said peripheral blood mononuclear cells;
   d) measuring L13 mRNA in said peripheral blood mononuclear cells;
   e) diagnosing the individual as being at risk for a relapse based on a ratio of measured FasL mRNA to L13 mRNA of 52.6 or less; and
   f) administering a multiple sclerosis treating drug to the individual diagnosed as being at risk of relapse.

6. The method of claim 5, further comprising repeating the steps a) to d) on the individual daily, weekly or monthly.

7. The method of claim 5 further comprising,
   measuring at least one of Response Gene to Complement-32 mRNA or IL-21 mRNA in the peripheral blood mononuclear cells;
   diagnosing the individual as being at risk for relapse based on a ratio of at least one of the measured Response Gene to Complement-32 mRNA to L13 mRNA of 1.27 or less or the measured IL-21 mRNA to L13 mRNA.

8. The method of claim 5, wherein said multiple sclerosis treating drug is glatiramer acetate or interferon-β.

9. A method for treating an individual with relapsing-remitting multiple sclerosis that is at risk for a relapse comprising the steps of:
   a) collecting a peripheral blood sample from the individual;
   b) isolating peripheral blood mononuclear cells from said peripheral blood sample;
   c) measuring IL-21 mRNA in said peripheral blood mononuclear cells;
   d) measuring L13 mRNA in said peripheral blood mononuclear cells;
   e) diagnosing the individual as being at risk for a relapse based on a ratio of IL-21 mRNA to L13 mRNA of 16.9 or greater; and
   f) administering a multiple sclerosis treating drug to the individual diagnosed as being at risk of relapse.

10. The method of claim 9, further comprising repeating the steps a) to d) on the individual daily, weekly or monthly.

11. The method of claim 9, further comprising:
    measuring at least one of Response Gene to Complement-32 mRNA or FasL in the peripheral blood mononuclear cells;
    diagnosing the individual as being at risk for relapse based on a ratio of at least one of the measured Response Gene to Complement-32 mRNA to L13 mRNA of 1.27 or less or the measured FasL mRNA to L13 mRNA of 52.6 or less.

12. The method of claim 9, wherein said multiple sclerosis treating drug is glatiramer acetate or interferon-β.

13. A method for treating an individual with relapsing-remitting multiple sclerosis that is at risk for a relapse, comprising, the steps of:
    a) collecting a peripheral blood sample from the individual;
    b) isolating peripheral blood mononuclear cells from said peripheral blood sample;
    c) measuring Response Gene to Complement-32 mRNA, FasL mRNA, IL-21 mRNA, and L13 mRNA in said peripheral blood mononuclear cells;
    d) diagnosing the individual as being at risk for a relapse based on a ratio of measured Response Gene to Complement-32 mRNA to L13 mRNA of 1.27 or less, measured FasL mRNA to L13 mRNA of 52.6 or less and measured IL-21 mRNA to L13 mRNA of 16.9 or greater;
    e) administering a multiple sclerosis treating drug to the individual diagnosed as being at risk of relapse.

14. The method of claim 13, further comprising repeating the steps a) to c) on the individual daily, wherein when at least one of the ratio of the measured Response Gene to Complement-32 mRNA to L13 mRNA is 2.52 or greater, the ratio of the measured FasL mRNA to L13 mRNA is 85.4 or greater or the ratio of the measured IL-21 mRNA to L13 mRNA is 11.9 or less from one day to the next, the individual will respond or is responding positively to said treatment.

15. The method of claim 13, further comprising repeating the steps a) to c) on the individual weekly, wherein when at least one of the ratio of the measured Response Gene to Complement-32 mRNA to L13 mRNA is 2.52 or greater, the ratio of the measured FasL mRNA to L13 mRNA is 85.4 or greater or the ratio of the measured IL-21 mRNA to L13 mRNA is 11.9 or less from one week to the next, the individual will respond or is responding positively to said treatment.

16. The method of claim 13, further comprising repeating the steps a) to c) on the individual monthly, wherein when at least one of the ratio of the measured Response Gene to Complement-32 mRNA to L13 mRNA is 2.52 or greater, the ratio of the measured FasL mRNA to L13 mRNA is 85.4 or greater or the ratio of the measured IL-21 mRNA to L13 mRNA is 11.9 or less from one month to the next, the individual will respond or is responding positively to said treatment.

17. The method of claim 13, wherein said multiple sclerosis treating drug is glatiramer acetate or interferon-$\beta$.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: forward primer for Response Gene to
      Complement-32

<400> SEQUENCE: 1
aggaacagct tcagcttcag                                               20

<210> SEQ ID NO 2
<211> LENGTH: 24
<212> TYPE: DNA
<213> ORGANISM: Artificial Sequence
<220> FEATURE:
<223> OTHER INFORMATION: reverse primer for Response Gene to
      Complement-32

<400> SEQUENCE: 2
gctaaagttt tgtcaagatc agca                                          24

<210> SEQ ID NO 3
<211> LENGTH: 20
<212> TYPE: DNA
<213> ORGANISM: Artificial Sequence
<220> FEATURE:
<223> OTHER INFORMATION: forward primer for Fas Ligand gene

<400> SEQUENCE: 3
gcccatttaa caggcaagtc                                               20

<210> SEQ ID NO 4
<211> LENGTH: 20
<212> TYPE: DNA
<213> ORGANISM: Artificial Sequence
<220> FEATURE:
```

<223> OTHER INFORMATION: reverse primer for Fas Ligand gene

<400> SEQUENCE: 4
atcacaaggc caccttctt                                                  20

<210> SEQ ID NO 5
<211> LENGTH: 20
<212> TYPE: DNA
<213> ORGANISM: Artificial Sequence
<220> FEATURE:
<223> OTHER INFORMATION: forward primer for cell division cycle protein
      2 homolog gene

<400> SEQUENCE: 5 tttttcagagc tttgggcact                                                20

<210> SEQ ID NO 6
<211> LENGTH: 20
<212> TYPE: DNA
<213> ORGANISM: Artificial Sequence
<220> FEATURE:
<223> OTHER INFORMATION: reverse primer for cell division cycle protein
      2 homolog gene

<400> SEQUENCE: 6
aggcttcctg gtttccattt                                                 20

<210> SEQ ID NO 7
<211> LENGTH: 19
<212> TYPE: DNA
<213> ORGANISM: Artificial Sequence
<220> FEATURE:
<223> OTHER INFORMATION: forward primer for ribosomal protein L13 gene

<400> SEQUENCE: 7
cgtgcgtctg aagcctaca                                                  19

<210> SEQ ID NO 8
<211> LENGTH: 19
<212> TYPE: DNA
<213> ORGANISM: Artificial Sequence
<220> FEATURE:
<223> OTHER INFORMATION: reverse primer for ribosomal protein L13 gene

<400> SEQUENCE: 8
ggagtccgtg ggtcttgag                                                  19

<210> SEQ ID NO 9
<211> LENGTH: 18
<212> TYPE: DNA
<213> ORGANISM: Artificial Sequence
<220> FEATURE:
<223> OTHER INFORMATION: forward primer for AKT1 viral oncogene

<400> SEQUENCE: 9
acgccaagga gatcatgc                                                   18

<210> SEQ ID NO 10
<211> LENGTH: 21
<212> TYPE: DNA
<213> ORGANISM: Artificial Sequence

```
<220> FEATURE:
<223> OTHER INFORMATION: reverse primer for AKT1 viral oncogene

<400> SEQUENCE: 10
ctccatgctg tcatcttggt c                                                    21
```